United States Patent [19]

Parish

[11] Patent Number: 5,086,054

[45] Date of Patent: Feb. 4, 1992

[54] NOVEL ARYLCYCLOALKANEPOLYALKYLAMINES

[75] Inventor: Daniel W. Parish, Sunnyvale, Calif.

[73] Assignee: SRI International, Menlo Park, Calif.

[21] Appl. No.: 560,446

[22] Filed: Jul. 31, 1990

[51] Int. Cl.[5] .................. A61K 31/445; A61K 31/33; C07D 265/30; C07D 295/22; C07D 211/06

[52] U.S. Cl. ............................. 514/239.2; 514/237.5; 514/237.8; 514/238.2; 514/238.8; 514/317; 514/319; 514/320; 514/323; 514/326; 514/422; 514/423; 514/424; 514/427; 544/158; 544/160; 544/161; 544/164; 548/527; 548/530; 548/537; 548/538; 548/539; 548/541; 548/542; 548/543; 548/205; 548/198; 548/196; 548/201; 546/208; 546/212

[58] Field of Search ............... 544/158, 160, 161, 164; 514/237.5, 237.8, 238.2, 238.8, 279.2

[56] References Cited

U.S. PATENT DOCUMENTS 4,634,713 1/1987 Werner et al. .................. 544/160

*Primary Examiner*—Johann Richter
*Attorney, Agent, or Firm*—Hana Dolezalova

[57] ABSTRACT

Novel arylcycloalkanepolyalkylamines useful as anti-psychotic, anti-ischemia, anti-stroke, anti-dementia and anti-convulsant agents. These arylcycloalkanepolyalkylamines are selective high-affinity ligands to the sigma binding-sites containing three basic units: arylcycloalkyl group, an amine group and an intermediate chain. Their preparation and use for treatment of psychoses, ischemia, stroke, dementia and convulsions are also disclosed.

20 Claims, 1 Drawing Sheet

Haloperidol o-Ditolylguanidine

N-Allylnormetazocine

Cyclazocine

Pentazocine

NOVEL ARYLCYCLOALKANEPOLYALKYLAMINES

BACKGROUND OF INVENTION

1. Field of the Invention

This invention relates to novel arylcycloalkanepolyalkylamines that are useful as anti-psychotic, anti-ischemia, anti-stroke, anti-dementia and anti-convulsant agents. In particular, this invention relates to arylcycloalkanepolyalkylamines that are selective high-affinity ligands to the sigma binding-sites and their preparation and use for treatment of psychoses, ischemia, stroke, dementia and convulsions. These selective, high affinity sigma ligands contain three basic chemical components: a) an arylcycloalkyl group, b) an amine group and c) an intermediate chain.

2. Related Disclosures

Psychoses are major mental disorders of organic and/or emotional origins characterized by derangement of the personality and loss of contact with reality. They are a serious problem facing society. People suffering from various psychotic states are often unable to exist on their own and require either institutionalization or home care and supervision, both of which are very costly to society.

Over the past 35 years, the development of various psychotropic drugs has produced major changes in the management of psychotic mental disorders. The use of these drugs has decreased the need for continuous or extended hospital care and allowed restoration of a patient's basic functioning to a level necessary for a satisfying and productive life.

The antipsychotic drugs include phenothiazines chlorpromazine, triflupromazine, mesoridazine, perphenazine, prochlorperazine and trifluoperazine; thioxanthenes chlorprothiaxine and thiothixine; dihydroindolone molindone; dibenzoxazepine loxapin; diphenylbutylpiperidine pimoside; and butyrophenones haloperidol and droperidol. Although these and other similar drugs are effective in the treatment of acute and chronic schizophrenia, depression, manic-depressive psychosis and other psychotic conditions, they are accompanied by a variety of undesirable and deleterious side effects. These side effects include drowsiness, sedation, hypotension, reduction of convulsive seizure threshold, ocular and skin pigmentation, photosensitization, hepatotoxicity, chronic cholestatic liver disease and cardiac arrhythmias. The extrapyramidal symptoms (EPS), such as akathisia, dystonia, tremors and rigidity, tardive dyskinesia, parkinsonism, etc., however, represent the most serious side-effect liability of the antipsychotic drugs. Because of the severity of such side effects, many patients avoid or refuse to use antipsychotic drugs and, when untreated, revert to their original psychotic conditions.

Thus, it would be extremely valuable to have available antipsychotic agents that are free of this undesirable side effect liability, especially that caused by EPS.

Receptors are specific, chemically defined sites on the surface of cells and are frequently classified according to their ability to bind certain ligands (compounds). When bound to a receptor, these ligands can act directly by stimulating or inhibiting normal receptor function, or indirectly by blocking the binding site and preventing normal (endogenous) ligand-binding. Many pharmacologically active agents act at the receptor level by either mimicking the action of an endogenous ligand (agonist) or by blocking the action of an endogenous ligand (antagonist).

Neurotransmitters are endogenous ligands that chemically affect the receptors on nerve cells or the organs innervated by these cells. Under normal physiological conditions, a certain level of neurotransmitter is released and/or present in the vicinity of its specific receptors. When the normal level of a neurotransmitter is disturbed, pathological conditions such as the various forms of psychoses, depression, schizophrenia, Parkinson's disease, Huntington's chorea, Grave's or Cushing's disease, etc., may develop.

Most known receptors have a developed pharmacology of agents that act as agonists or antagonists. For example, antagonists are known that block the actions of the neurotransmitters dopamine, adrenalin, noradrenalin and acetylcholine. Many neurotransmitter agonists and antagonists have been identified and are described in the neuroscientific literature.

Despite extensive pharmacological research and the continuing development of progressively more sophisticated laboratory techniques, many receptor systems and/or their biological effects remain unknown. The availability of selective high-affinity ligands greatly facilitates the determination of a particular receptor's biological role. Such ligands can also be useful for treating pathological conditions arising from the dysfunction of their target receptor system. Thus, new compounds that can specifically affect the function of known receptor systems are always in demand.

The principal antipsychotic neuroleptic drugs currently clinically employed act as dopamine D-2 receptor antagonists. This receptor antagonism is believed to mediate the therapeutic antipsychotic actions as well as the serious EPS side-effects of the neuroleptics. Drugs with high affinities for the D-2 subclass of postsynaptic dopamine receptors are known to attenuate the positive symptoms (e.g., hallucinations, delusions, and formal thought disorder) of schizophrenia. Such activity has led to the hypothesis that schizophrenia is a consequence of hyperdopaminergic transmission [*FASEB*, 3:1869 (1989)].

Since known neuroleptic drugs are only palliative and are accompanied by prevalent, serious side effects, a significant effort has been directed toward the development of new antipsychotic drugs that might act in a novel fashion. Recent discoveries suggest that other, non-dopaminergic mechanisms also play a role in the development of schizophrenic pathology and other psychoses. For example, the α-adrenoceptor, β-adrenoceptor, serotonin (5-HT), muscarinic acetylcholine, and lately phencyclidine (PCP) and sigma (σ) receptors have been implicated in various psychotic symptoms. The existence of alternate mechanisms makes possible the development of new intervention strategies for treatment of schizophrenia with reduced EPS liability.

Animal behavioral paradigms, predictive of antipsychotic efficacy, identified a number of candidates that may lack the side effects associated with typical neuroleptic therapy [*Eur. J. Pharmacol.*, 155:345 (1988)]. When evaluated at dopamine D-2, 5-HT, α- and β-adrenoceptor, muscarine acetylcholine, PCP and sigma receptors, these compounds had a sole common feature; high affinity for σ receptors. Two of these drugs, rimcazole and remoxipride, which were shown in clinical trials to display clinical antipsychotic effects, are both potent and selective σ receptor ligands. Based on these findings, it has been suggested that inhibitors of σ receptors may act as antipsychotic agents.

The role of sigma receptors in mediating psychoses has been investigated for compounds that share an affinity for this receptor including the benzomorphans such as n-ally-normetazocine and cyclazocine, PCP, and antipsychotic drugs like haloperidol. The clinically effective neuroleptic haloperidol is a potent dopamine D-2 receptor antagonist, but at the same time possesses a high affinity for the σ site [Neurology, 38:961 (1988)].

PCP (1-(1-phenylcylohexyl)piperidine) is a psychomimetic drug with diverse biochemical effects in the central nervous system (CNS) and potent behavioral responses. Specific PCP receptors have been described in the brain, having a pharmacological selectivity and potency corresponding to the behavioral effects of PCP. PCP is known to influence transmitter metabolism in several different CNS regions, to alter gross motor activity and spatial alternation performance and to induce stereotypic movements [Synapse, 1:497 (1987)]. In humans, PCP causes psychotic reactions such as hallucinations, thought disorders and paranoid delusions similar to an acute schizophrenic episode.

Sigma receptors were identified based on the actions of ((±)-N-allylnormetazocine and related benzomorphan alkaloids. [J. Pharmacol. Exp. Ther., 197:517 (1976)]. They are distinguished on the basis of the following four characteristics: (a) stereoselectivity for dextrorotatory benzomorphans; (b) insensitivity to naloxone; (c) high affinity for haloperidol and (d) insensitivity to dopamine and apomorphine. Ligands that bind to σ receptors are haloperidol (4-[4-(p-chlorophenyl)-4-hydroxypiperidino]-4'-fluorobutyrophenone); (+)-3-PPP ((+)-3-(3-hydroxyphenyl)-N-(1-propyl)-piperidine), DTG (1,3-di-o-tolylguanidine); dextrallorphan; and benzomorphans such as N-allylnormetazocine (NAN), pentazocine (2-dimethylallyl-5,9-dimethyl-2-hydroxy-benzomorphan), and cyclazocine (3-(cyclopropylmethyl)-1,2,3,4,5,6-hexahydro-6,11-dimethyl-2,6-methano-3-benzazocin-8-ol). Structures of several sigma receptor ligands are shown in FIG. 1.

Based on these observations, the conclusion was reached that σ receptors are non-dopaminergic, non-opioid receptors that bind antipsychotic drugs as well as the (+) enantiomers of benzomorphans.

Two distinct populations of sigma receptors have been identified and labeled on $\sigma_p$- and $\sigma_h$-receptors. The haloperidol-sensitive $\sigma_h$ receptor sites exhibit a drug selectivity pattern and a brain distribution that differs from phencyclidine (PCP) - sensitive $\sigma_p$ receptors, dopamine receptors and all other known classes of receptors. Henceforth, the term "σ receptor" will refer to the haloperidol-sensitive σ receptor ($\sigma_h$).

The σ receptors are found in many brain areas involved in the control of movement. The observation that microinjections of DTG into the red nucleus and substantia nigra produce vigorous contralateral circling behavior, suggests that σ binding sites represent biologically functional receptors that are active in the neural control of movement [Neurology, 38:961 (1988)].

One high-affinity, σ-selective antipsychotic agent, rimcazole (cis-9-[3-(3,5-dimethyl-1-piperazinyl)propyl]-carbozole), was shown to antagonize climbing behavior in mice without producing the cataleptic state typically associated with the induction of EPS side effects. Unlike classical neuroleptics, rimcazole did not influence conditioned avoidance responses in rat. Also unlike classical neuroleptics, rimcazole did not exert its action at the level of postsynaptic dopamine receptors in the mesolimbic area. However, rimcazole was able to competitively inhibit specific binding of the σ receptor ligand NAN to specific membranes prepared from rat spinal cord and brain.

Previous attempts have been made to determine structural requirements for the interaction of PCP analogs with σ receptors. PCP analogs with an increased distance between the phenyl and piperidine rings show an increased affinity for σ receptors, at the expense of PCP receptor affinity [FASEB, 4:A359 (1990)].

From the literature cited above, it is clear that σ receptor dysfunction may be a naturally occurring pathogenic mechanism of psychosis in humans. Consequently, selective high-affinity σ receptor ligands may be valuable for treatment of psychotic symptoms such as delusions, hallucinations, depersonalization, dysphoria, affective liability, etc. They may also be effective against other conditions linked to σ receptor function such as ischemia, stroke, dementia and cocaine-induced convulsions. These ligands would be highly selective for σ receptors; they would not act on other receptors at antipsychotic doses, including PCP receptors; they would have potent antipsychotic therapeutic properties; and they would not produce undesirable side effects.

The current invention concerns a group of selective high affinity σ receptor ligands that are effective as antipsychotics, antiischemics and anticonvulsants, which do not possess undesirable side-effects.

SUMMARY

One aspect of this invention relates to compounds of the formula

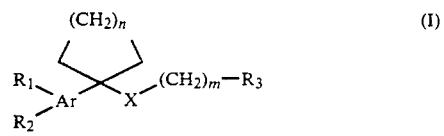

(I)

and their pharmaceutically acceptable salts; wherein

Ar is aryl;

R₁ and R₂ are independently selected from the group consisting of hydrogen, hydroxy, lower alkyl, cycloalkyl, alkoxy, nitro, thio, halo amino, amido, azido or isothiocyanato;

R₃ is amine;

X is ester, ether, ketone, amide, thioketone, thioamide, thioether or thioester;

n is 2, 3, 4 or 5;

m is 1, 2, 3, 4 or 5.

Another aspect of this invention relates to the method of preparation of the above-mentioned compounds. Still another aspect of this invention relates to the method of use of the compounds of the current invention for treatment of psychoses, ischemia, stroke, dementia and convulsions.

DETAILED DESCRIPTION OF THE INVENTION

Figure 1:
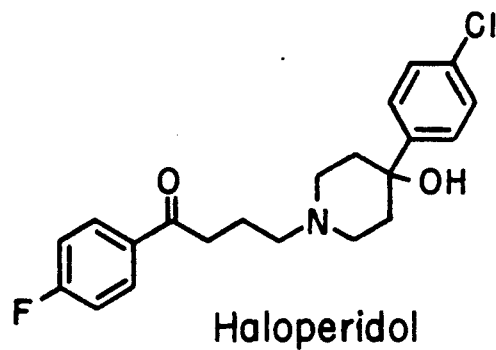
FIG. 1 shows chemical structures of several sigma receptor ligands.
Figure 1:
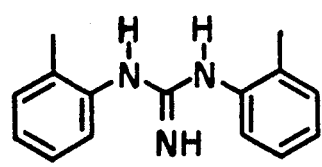
Figure 1:
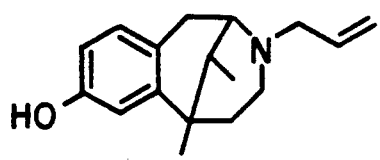
Figure 1:
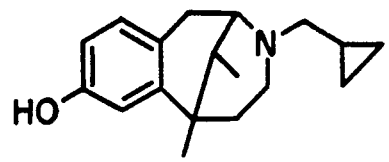
Figure 1:
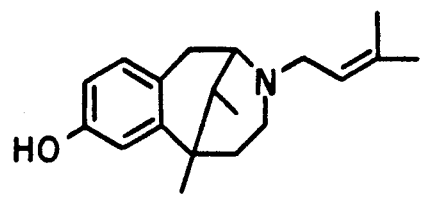

This invention relates to the preparation and use of arylcycloalkanepolyalkylamines that are selective high-affinity sigma receptor ligands useful as antipsychotic, antiischemic and anticonvulsants agents or in treatment of all diseases or conditions caused by σ receptor dysfunction.

These compounds are represented by the general formula

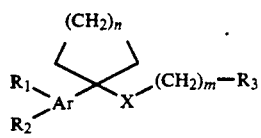

and their pharmaceutically acceptable salts; wherein
Ar is aryl;
$R_1$ and $R_2$ are independently selected from the group consisting of hydrogen, hydroxy, lower alkyl, cycloalkyl, alkoxy, nitro, thio, halo, amino, amido, azido or isothiocyanato;
$R_3$ is amine;
X is ester, ether, ketone, amide, thioketone, thioamide, thioether or thioester;
n is 2, 3, 4 or 5;
m is 1, 2, 3, 4 or 5.

Definitions

Hereinafter:

"Sigma or σ receptor" means binding site possessing the following four characteristics: (a) stereoselectivity for dextrorotatory benzomorphans; (b) insensitivity to naloxone; (c) high affinity for haloperidol; and (d) insensitivity to dopamine and apomorphine.

"IC50" values mean concentrations required to inhibit 50% of radioligand binding to a receptor.

"Lower alkyl" means a linear or branched saturated or unsaturated hydrocarbon chain containing from 1–6 carbon atoms, such as for example, methyl, ethyl, propyl, isopropyl, butyl, isobutyl, tertiary butyl, etc.

"Cycloalkyl" means a saturated or nonsaturated monocyclic hydrocarbon of 3–7 carbon atoms such as cyclopropane, cyclobutane, cyclopentane, cyclohexane, cycloheptane and their unsaturated derivatives.

"Aryl" means compound whose molecules have an aromatic ring structure, such as benzene, naphthalene, phenanthrene, anthracene, pyridine, thiophene, furan, imidazole, thiazole, quinoline, isoquinoline, indole, benzofuran, etc., i.e., either carbocyclic, heteroaromatic, or polynuclear aromatic rings.

"Alkoxy" means 0-lower alkyl, as defined above.

"Halo" means fluoro, chloro, iodo or bromo.

"Amine" means cyclic or acyclic amine such as pyrrolidine, piperidine, morpholine, diethylamine, dimethylamine and other primary, secondary, tertiary or quaternary amines.

"Pharmaceutically acceptable salts" means those salts that retain the therapeutic properties of the free bases and that are neither biologically nor otherwise undesired, formed with, for example, inorganic acids such as hydrochloric acid, hydrobromic acid, sulfuric acid, nitric acid or phosphoric acid, or organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, etc.

Preparation Procedures

Alkylamines of the current invention are prepared according to the Reaction Scheme I.

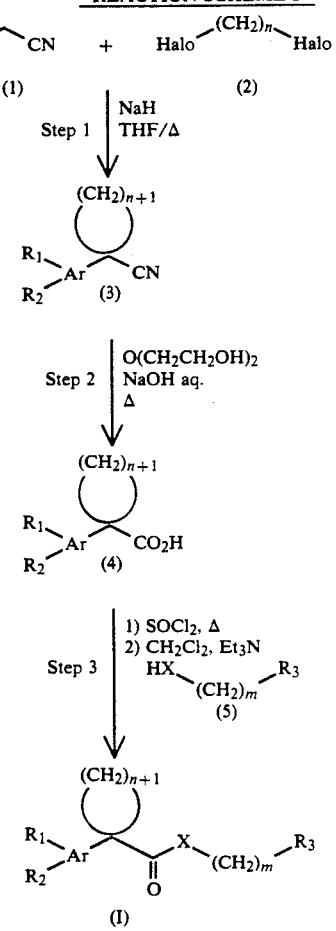

REACTION SCHEME I

Compounds of formula (I) are prepared by a three step procedure.

Step 1.

Substituted or unsubstituted aryl nitrile compounds (1), such as for example, phenylacetonitrile, dimethylphenylacetonitrile, methoxy or ethoxyphenylacetonitrile, thiophenylacetonitrile, and other arylnitriles having $R_1$ and $R_2$ substituents independently selected from hydrogen (unsubstituted aryl) or hydroxy, lower alkyl, cycloalkyl, alkoxy, nitro, thio or halo, are commercially available or prepared by methods known in the art.

Aryl (1) is reacted with a dihaloalkyl (2) such as 1,4 or 1,5 dibromoalkyl or dichloroalkyl in the presence of a hydride. The hydride, such as sodium, potassium or calcium hydride, preferably 60% sodium hydride (dispersion in mineral oil) in amount from 1 to 5 moles, preferably 2.2 moles, is suspended in an organic solvent such as ethers tetrahydrofuran, tetrahydropyran, 1,4-dioxane, furan or propylene oxide, preferably in 1–4 liters of tetrahydrofuran, preferably in around 2.5–3 liters. The mixture of tetrahydrofuran with sodium hydride is brought to reflux under inert gas atmosphere, preferably under Argon, and a mixture of dihaloalkyl (2) and aryl nitrile (1) in ratio from 1:0.1 to 0.1-1 is added slowly dropwise to the refluxing solvent over the period of 3-10 hours, preferably 5 hours, under constant stirring which is continued at reflux temperature for 10-24 hours, preferably 16 hours. Excess hydride is decomposed with water and the solvent is decanted and evaporated to provide arylcycloalkanecarbonitrile compound (3).

Compound (3) prepared by the above procedure is then submitted to step 2.

Step 2.

Arylcycloalkanecarbonitrile (3) is hydrolyzed by heating in the presence of a hydroxylated ether, preferably 2-hydroxyethyl ether, containing an aqueous strong base such as sodium hydroxide, potassium hydroxide, ammonium hydroxide and the like, preferably 40% potassium hydroxide, to yield arylcycloalkanecarboxylic acid (4).

Arylcycloalkanecarbonitrile (3) in amount from 100-1000 mmol, preferably around 260 mmol is added to 100-1000 ml of a mixture of an ether, such as tetrahydrofurane, tetrahydropyrane, ethyl ether, 1,4-dioxane, furan and the like, preferably 249 ml of 2-hydroxyethyl ether with the 40% aqueous base, preferably 300 ml of potassium hydroxide, to form a heterogeneous solution. The resulting mixture is heated, preferably to reflux temperature for 5-30 hours, preferably for about 16 hours. The mixture is then cooled for 10 minutes to 2 hours, preferably for about 1 hour and the now homogeneous solution is poured into 1-5 liters of water, preferably 2 liters of water and extracted with an aliphatic ether, such as ethyl ether, propyl or isopropyl ether, propylene dioxide, ethylene oxide, furan, 1,4-dioxane and the like, preferably it is extracted four times with 100-500 ml of 1,4-dioxane. The aqueous layer is removed and adjusted to acidic pH, preferably around pH 1 by addition of concentrated strong acid such as hydrochloric acid, sulfuric acid, hydrobromic acid, phosphoric acid and the like, preferably by addition of aqueous hydrochloric acid in amount needed to lower the pH to pH 1, and the whole mixture is extracted several times with an ester such as methyl formate, ethyl formate or propyl formate, methyl acetate, ethyl acetate, butyl acetate, propyl acetate, benzyl acetate, and the like, preferably with ethyl acetate. Ethyl acetate extracts are combined and dried over a desiccating substance, such as sodium sulfate. The solvent is removed under vacuum. Flash chromatography on silica gel or any other separation method is performed. The column is eluted with any suitable solvent, such as chlorinated hydrocarbons, methylene chloride, ethylene chloride, ethyl chloride, pentyl chloride, chloroform, tetrachloroethane and the like, preferably with methylene chloride. The eluant is recrystallized in an organic solvent mixture, such as a mixture of the ester with saturated, unsaturated or aromatic hydrocarbon, such as esters named above, preferably ethyl acetate with pentane, butane, hexane, cyclohexane, octane, hexane, dodecane, benzene, toluene, pentene, cyclohexene and the like, preferably hexane, to provide carboxylic acid compound (4).

Step 3.

Arylcycloalkane carboxylic acid (4) is converted to an acid chloride which is converted to compound (I) by reaction with compound (5), polyalkylaminoalkanol dissolved in a chlorinated hydrocarbon containing an amine.

Compound (5) comprises 1-5 $CH_2$ groups connecting an amine $R_3$ with XH substituent. Amine $R_3$ may be any aliphatic amine, aromatic amine, or unsaturated amine, such as primary, secondary or tertiary amine represented by following exemplary compounds, propylamine, isopropylamine, cyclohexylamine, aniline, toluidine, allylamine, ethylenediamine, dimethylamine, diethylamine, pyrrole, pyridine, piperidine, pyrrolidine, morpholine, and the likes. XH substituent is hydroxy, thiol, amino, halo, etc. Compound (5) is generally commercially available or may be prepared by methods known in the art.

Compound (4) is dissolved in 1-5, preferably 2.5, equivalents of a reagent that is able to provide the chloride, such as thionyl chloride, phosphorus trichloride, phosphorus pentachloride, or oxalyl chloride, preferably thionyl chloride, and heated at reflux temperatures for 5-30 hours, preferably for 16 hours. Excess thionyl chloride is removed under aspirator vacuum and the resulting golden-yellow oil is flushed with an inert gas, such as helium or argon, preferably argon for 10 minutes to 3 hours, preferably for 1 hour. The acid chloride of compound (4), obtained as crude semicrystalline oil, is dissolved in a polychlorinated hydrocarbon such as those listed above, preferably in methylene chloride in an amount from 1-10 ml/g of acid, preferably 5 ml/g of acid, containing 0.5-2 equivalents of a tertiary amine such as any tryalkylamine, pyridine, or the like, preferably 1.1 equivalent of triethylamine. Compound (5) is slowly added to the mixture of polychlorinated hydrocarbon with the amine, to avoid a sudden exotherm. Within 3-60 minutes, usually around 5-10 minutes, a precipitate begins to form in the solution. The solution is stirred for 8-40 hours, preferably for about 16 hours at temperature from 15°-40° C., preferably at room temperature and then it is diluted with polychlorinated hydrocarbon, such as methylene chloride in amount from 5-100 ml per g of acid, preferably around 30 ml per g of acid and subsequently washed once with a base, preferably with 0.5M aqueous potassium hydroxide. Then, the solvent is removed under reduced pressure. The resulting crude compound (I) is purified by flash chromatography on silica gel or by any other means suitable for such purposes and known in the art. The desired fraction is collected and the solvent is removed. The resulting compound is pure arylpolyalkane polyalkylamine carboxylate, ether, ester, amide, thioester or ketone compound (I).

Using procedures described above, a series of compounds derived from the generic formula were synthesized as shown in Tables 1-4.

Table 1 summarizes potencies at $\sigma$ and PCP receptors of various PCP derivatives with a methylene, ethylene or carboxyl ethylene insertion between the cyclohexyl and amine groups of phencyclidine and several of its analogs. For each compound with such an insertion, analogs containing various phenyl substituents, amine groups, and cycloalkyl rings, were also synthesized.

Phencyclidine (1) was used as standard compound. Methylene, ethylene, and carboxyl ethylene were inserted between the cyclohexyl and amine of phencyclidine (PCP) compound (1) and several of its known analogs, which also served as comparative standards. These analogs included 1-(1-phenylcyclohexyl)pyrrolidine (PCPY) (5), 4-(1-phenylcyclohexyl)morpholine (PCM) (10), N,N-diethyl-1-phenylcyclohexylamine (PCDEA) (13), and N,N-dimethyl-1-phenylcyclohexylamine (PCDMA) (17). The structures of compounds 2-4, 6-9, 11-12, 14-16 and 18-20, which are the respective analogs of PCP, PCPY, PCM, PCDEA and PCDMA are shown in Table 1. The affinities of these compounds for σ and PCP receptors were determined according to the procedure described in Example 4.

As seen from Table 1, insertion of methylene, (compound 2), ethylene (compound 3), or carboxyl ethylene (compound 4), into PCP (compound increased the potency of the compound in the σ receptor assay, whereas concomitantly reduced the potency in the PCP receptor assay. For example, insertion of methylene (m=1) into PCP (1), yielded compound (2) having increased potency for σ receptors about 80 times while at the same time it decreased the potency for PCP receptors approximately 40 times. Insertion of both ethylene (m=2) and carboxyl (X=C(O)O), as seen in compound (3), increased the potency for σ receptors more than 300 times and decreased potency for PCP receptors about 700 times. Quarternization of compound (3), yielding compound (4), drastically reduced potency for both σ and PCP receptors. Insertion of methylene into the basic PCP-like compounds PCPY (5), PCM (10), PCDEA (13) and PCDMA (17) rendered compounds, (6), (11), (14) and (18), having increased potency for σ receptors. Compounds (11), (14) and (18) were inactive in the PCP receptor assay.

Insertion of ethylene alone (m=2) into PCPY (5), yielding compound (7) decreased the potency in the PCP receptor assay relative to standard PCPY compound (5). However, such insertion increased the potency for σ receptors approximately 30-fold relative to PCPY (5).

All derivatives shown in Table 1 wherein X is carboxyl and m=2, such as compounds (3), (4), (8), (9), (12), (15), (16), (19) and (20) were inactive in the PCP assay while their σ receptor potency increased, relative to the standard parent compounds. For example, compound (8) had an IC50 of 5 nM in the σ assay and about 64,000 nM in the PCP assay. Similarly, compounds (3), (12), (15) and (19) were all very potent in the σ assay, but were very weak or inactive in the PCP assay.

From the results summarized in Table 1, it is clear that the PCP derivatives containing alkylene wherein m=1-5 inserted between the cycloalkyl ring wherein n=2-5 and amine R3, possess efficiently modified molecular properties with respect to their binding preference for PCP and σ receptors. Insertion of either methylene or ethylene into the standard parent compound (1), (5), (10), (13), or (17) substantially decreased the derivative compound's affinity for PCP receptors and substantially increased its affinity for σ-receptors. When these compounds were modified to contain a component wherein X is carboxyl, such as in compounds (3), (8), (12), (15) and (19) their potencies for PCP receptors were negligible, while their potencies for σ receptors were very high. For example, compound (12) possesses high potency (IC50=44 nM) at σ receptors while its potency for PCP receptors was lower than 100,000 nM. In addition, its IC50 in many other receptor binding systems was also affected. As shown in Table 4, the potency of compound (12) for dopamine D2 receptors was 55,702 nM, for muscarinic acetylcholine receptor was 13,953 nM, for 5-HT$_2$ was 18,748 nM, and for $\alpha_1$- or $\beta$-adrenoceptor was higher than 100,000 nM and 200,000 nM, respectively.

Quarternization of the amines, as in compounds (4), (9), (16) and (20), shown in Table 1, effectively reversed the potency for σ receptors but did not increase potency for PCP receptors.

To investigate the effect of various aryl ring substituents on the potencies at σ and PCP receptors, a series of compounds having the same or different substituents $R_1$ and $R_2$ were prepared. The individual chemical entities and their potencies with respect to σ and PCP receptors are summarized in Table 2. Results varied with each starting compound.

The σ-receptor potencies of derivatives with piperidine as the amine group, (compounds 21-28), were not dramatically altered after various substitutions at the phenyl ring, compared to their unsubstituted counterpart, compound (2). The exception was the hydroxy substitution (compound 21) which diminished binding to σ receptors. In the piperidine series, the compound (25) having a chloro substituent seemed to be the most potent at σ receptors, having IC50 71 nM, but the least specific since it also showed some potency at PCP receptors. 4-methyl, 4-nitro, 3-methoxy 4-methoxy and 3,4-methoxy substitution on the phenyl ring (compounds 23, 24, 26, 27 and 28) results in slightly lower σ receptor potencies, but substantially increases selectivity for σ receptors.

The group of derivatives wherein $R_3$ is pyrrolidine, namely compounds 29-35, showed increased potency at σ receptors against their control compound (6) with varying results at PCP receptors. In this group, the effect of hydroxy substitution on σ receptor affinities was position dependent. 3-hydroxy substitution, compound (29), had only slight effect on σ receptor potency and its selectivity for σ receptors was poor. Although 4-hydroxy substitution, compound (30), did not improve potency as much as the 3-hydroxy derivative, it considerably improved selectivity for σ receptors; compound (30) was inactive at PCP receptor sites. Similarly to the piperidine-containing derivatives, 4-nitro (31) and 4-methoxy (34) substituted compounds were both somewhat potent and very selective for σ receptors; being inactive at PCP sites.

In the group containing morpholino, (36-38) phenyl ring substitution eradicated the potencies at both σ and PCP receptors.

The compounds wherein the amine is dimethylamine (18) that were substituted with nitro, methyl, methoxy or other substituents, were not very potent, but were selective for σ receptors, being essentially inactive at PCP sites. The compound wherein the amine is diethylamine (14) showed reasonable potency at σ receptors after 4-nitro substitution and remained inactive at PCP receptors.

Double substitution on phenyl ring in positions 3- and 4-, such as in compounds (28), (35), (43) showed poor to reasonable potency at σ sites and high selectivity for σ receptors. The morpholino compound (38) was the exception being essentially inactive in both σ and PCP binding assays.

In conclusion, aryl ring substitution can positively affect both the potency and selectivity of these compounds. Nitro and methoxy substituents were generally better than hydroxy substituents with respect to both potency and selectivity. Chloro substituents provide good potency but small selectivity. All morpholine-containing compounds were inactive at PCP receptors and aryl substitution completely eliminated any activity at σ receptors as well.

Potencies at σ and PCP receptors of derivatives with various cycloalkyl ring sizes were investigated and the results are summarized in Table 3.

The studied derivatives were compounds wherein amine $R_3$ was either piperidine or pyrrolidine, wherein X was zero or carboxyl, m was 1 or 2 and n was 0 or 2, i.e., the cycloalkyl was either cyclopropyl compounds (45) and (47) or cyclopentyl compounds (44) and (46). In these studies, lower cycloalkyl replaced cyclohexyl of the compounds shown in Tables 1 and 2. In all cases except for the pyrrolidine-containing compound (6), which was already inactive at PCP receptors, reduction in ring size decreased the potency at both σ and PCP receptors.

In still another set of experiments, selected compounds having an IC50 of <100 nM at σ receptors and possessing low potency at PCP receptors were examined in various receptor binding assays. Binding affinities to σ, PCP, dopamine D-2, muscarinic acetylcholine, 5-HT$_2$, $\alpha_1$- and $\beta$-adrenergic receptors were determined according to Example 5. The compounds thus selected for this study were all derivatives with carboxyl ethylene insertion. These included compound (3), (8), (12), (15) and (19) having the same chemical formulas as shown in Table 1.

The results, summarized in Table 4, indicate that except for compound (12), all other derivatives have appreciable potencies at several receptors. Specifically compounds (3), (8), (15) and (19) were quite potent at muscarinic acetylcholine receptors, having IC50 values 46, 23, 189 and 750 nM, respectively. These four derivatives also showed moderate potencies at dopamine D-2 and 5-HT$_2$ receptors. Compound (12), however, was very selective towards σ receptors being at least 300, 400 and 1200 fold more potent at σ receptors than at muscarinic acetylcholine, 5-HT$_2$, and dopamine D-2 receptors, respectively.

Compound (12), namely 2-(4-morpholino)ethyl 1-phenylcyclohexane-1-carboxylate, therefore, is the most selective σ ligand examined in this study. Although its potency at σ receptors is not as great as other known σ ligands, such as for example haloperidol, the potency of compound (12) is comparable to other σ ligands such a DTG and (+)-3-PPP shown in FIG. 1. The primary advantage of compound (12) over other known σ ligands is its high selectivity for σ receptors as evidenced by a minimal cross-activity with other receptors. The relative inactivity of compound (12) at PCP receptors and the other assayed receptor systems suggests that the compound (12) may be the most selective σ ligand found to date and therefore may be helpful in elucidating the possible pharmacological and physiological roles of σ receptors. In addition, compound (12) may be useful as a therapeutic agent for treatment of diseases and conditions connected with the dysfunction of the σ-receptor system.

There are two primary requirements for a drug to be useful receptor-targeted therapeutic agent. First, the drug must have a reasonably high potency at the receptor site of interest. Second, it must be selective for that particular receptor. There are many drugs that are either selective but not very potent or that are very potent but not selective.

In the first case, the use of the selective drug with low potency would require administering a large amount of drug to a patient in order to achieve any therapeutic benefit. This would be very costly and the use of such large amounts of these drugs might lead to undesirable side effects such as hepatotoxicity or nephrotoxicity.

In the second case, the high potency and low selectivity is equally bad. When the compound is highly potent, only a small amount of the compound is required to occupy the receptor binding site. Unfortunately, when the compound lacks selectivity, it may elicit a response from other receptors and thus may, while conferring benefit via one receptor, simultaneously elicit deleterious side effects via other receptors. Such results are highly undesirable.

Evaluation of the studies summarized in Tables 1–4 shows that increasing the distance between aryl and amine groups in phencyclidine-like compounds enhances their potency at σ receptors and reduces their potency at PCP receptors. These observations are in agreement with the prediction by several molecular modeling studies [Eur. J. Pharmacol., 144:231 and Mol. Pharmacol., 34:863 (1988)]. With the exception of a potential difficulty with DTG, these studies have indicated that selective σ ligands are usually "stretched" in conformation as opposed to being "globular". According to these studies, a globular form fits PCP receptors much better than σ receptors. This invention confirms that insertions of methylene, ethylene, and carboxyl ethylene into phencyclidine, which may make the derivatives more "stretched" than the parent compounds, improves their potencies at σ receptors and tends to decrease their potencies at PCP receptors.

From the studies performed in support of this invention, the structural and spatial requirements for selective, high-affinity σ receptor ligands appears to be as follows.

The structure of the σ ligands contains three basic units: 1) a hydrophobic cluster such as arylcycloalkyl group; 2) an amine group; and 3) an intermediate chain. Within each basic unit, certain structural requirements also affect the affinity and selectivity. Thus, changes in aryl group substituents, cycloalkyl ring size, amine group, and the presence and length of the intermediate chain, changes potency at σ receptors and affects the selectivity of a compound for σ receptors.

Based on these findings, compounds that are selective high-affinity σ receptor ligands have been designed. So far, the best compound was found to be 2-(4-morpholino)ethyl 1-phenylcyclohexane-1-carboxylate hydrochloride (12).

UTILITY

Compounds of the current invention are selective high affinity σ-receptor ligands that are inactive at the PCP and other known receptors. These selective ligands are useful in treatment of diseases or conditions that are caused by dysfunction of the σ receptor system and may be designed in a way to avoid undesirable deleterious side effects.

Conditions caused by dysfunction of the σ receptor may be treated or corrected by compounds of this invention administered in any suitable pharmaceutical form, formulation and dosage as customary in the pharmaceutical sciences. The compounds of this invention may be formulated as pills, tablets, capsules, drops or such other forms as useful for oral administration, or they can be prepared in solutions for parenteral intravenous, intramuscular, intraperitoneal, and subcutaneous administration, or in any other form.

The compounds may be useful as antipsychotics, tranquilizers, antiischemics, antistroke, antidementia agents, and anticonvulsants, particularly for treatment of convulsions connected with cocaine use and overdose.

The following examples are intended to illustrate the current invention but are in no way to be interpreted as limiting the invention to the compounds or procedures described in the Examples.

METHODS AND MATERIALS

Nuclear magnetic resonance (NMR) spectra were recorded on a Varian Associates EM-360 or EM-390 spectrometer; chemical shifts are reported in parts per million ($\delta$) from an internal tetramethylsilane standard. Splitting patterns are designated as follows: s, singlet; d, doublet; t, triplet; q, quartet; m, multiplet; br, broad. Infrared (IR) spectra were obtained on a Perkin-Elmer Model 1420 spectrophotometer. Melting points were determined on a Fisher-Johns or Mel-Temp melting point apparatus and are uncorrected. Analytical thin-layer chromatography (TLC) was performed on Analtech Uniplate silica gel GF (scored 10×20 cm, 250 μm). Flash Column chromatography was performed on silica gel reagent (230–400 mesh) obtained from American Scientific Products. Microanalyses were performed by Desert Analytics Organic Microanalysis, Tucson, AZ 85717.

All radiochemicals were purchased from New England (Boston, Mass.) with the following specific activity: [$^3$H]d-SKF-10,047, 30.8 or 59 Ci/mmole; [$^3$H]TCP, 60 Ci/mmole; $^3$H]spiroperidol, 22 Ci/mmole; [$^3$H]QNB, 43.9 Ci/mmole; $^3$H]prazosin, 26 Ci/mmole, and [$^{125}$I]-pindolol, 2200 Ci/mmole. Haloperidol was obtained from McNeil Labs (Fort Washington, Pa.). Prazosin and 1-propranolol were obtained from Pfizer (CT) and Ayerst (NY) respectively. All chemicals used were of reagent grade.

EXAMPLE 1

Preparation of Arylcycloalkanecarbonitriles

This example illustrates the preparation of arylcycloalkanecarbonitriles (3).

Sodium hydride (60% dispersion in mineral oil; 2.2 mol) was washed several times with hexane and suspended in THF (2.75 l) which was then brought to reflux under Argon. A mixture of dibromoalkane (1.05 mol) and a substituted benzyl cyanide (1.0 mol) was added dropwise to the refluxing THF solution over 5 hours. Stirring was continued at reflux for 16 hours. Excess hydride was then decomposed by the cautious addition of water, and the THF solution was decanted and evaporated to yield a cloudy, brown, amorphous solid. The solid was dissolved in hexanes or dichloromethane (800 ml), washed with water (3×1 l), dried over Na$_2$SO$_4$, and clarified by passing through a bed of diatomaceous earth (Celite); the solvents were then removed at reduced pressure. The resulting oil was vacuum-distilled to provide the desired product.

Following compounds were prepared:

1-Phenylcyclopentanecarbonitrile. The distilled yield was 88.64 g (52%) as a clear, colorless oil: bp 90°–100° C. (0.20 mmHg); $^1$H NMR (CDCl$_3$) $\delta$7.44 (m, 5H, ArH), 2.66–1.86 (m, 8H, cyclic-CH$_2$).

1-(3-Methoxyphenyl)cyclopentanecarbonitrile. The distilled yield was 168 g (83%) as a clear, colorless oil: bp 124°–128° C. (0.50 mmHg); $^1$H NMR (CDCl$_3$) $\delta$7.20 (m, 4H, ArH), 3.87 (s, 3H, OCH$_3$), 2.67–2.03 (br m, 8H, cyclic-CH).

1-Phenylcyclohexanecarbonitrile. The distilled yield was 160 g (80%) as a clear, colorless oil: bp 98°–105° C. (0.40 mmHg); $^1$H NMR (CDCl$_3$) $\delta$7.5 (m, 5H, ArH), 1.9 (br m, 10H, cyclic-CH$_2$).

1-(3-Methoxyphenyl)cyclohexanecarbonitrile. The distilled yield was 63.0 g (88%) as a clear, viscous, light yellow oil: bp 110°–120° C. (0.07 mmHg); $^1$H NMR (CDCl$_3$) $\delta$6.99 (m, 4H, ArH), 3.84 (s, 3H, OCH$_3$), 1.78 (m, 10H, cyclic-CH$_2$).

1-(4-Methylphenyl)cyclohexanecarbonitrile. The distilled yield was 100.5 g (73%) as a clear, colorless oil: bp 185°–120° C. (0.40 mmHg); $^1$H NMR (CDCl$_3$) $\delta$7.32 (m, 4H, ArH), 2.36 (s, 3H, CH$_3$), 2.33–1.22 (br m, 10H, cyclic-CH$_2$).

1-(3,4-Dimethoxyphenyl)cyclohexanecarbonitrile. The distilled yield was 100.5 g (73%) as an oil that crystallized upon cooling: bp 156°–160° C. (0.48 mmHg); mp 68°–69° C.; $^1$H NMR (CDCl$_3$) $\delta$6.98 (m, 3H, ArH), 3.94 (d, 6H, OCH$_3$), 2.31–161 (br m, 10H, cyclic-CH$_2$).

1-(2-Thienyl)cyclohexanecarbonitrile. The distilled yield was 61.0 g (79%) as a clear, colorless oil: bp 105°–110° C. (0.10 mmHg); $^1$H NMR (CDCl$_3$) $\delta$7.08 (m, 3H, ArH), 2.70–2.15 (br m, 10H, cyclic-CH$_2$).

1-(1-Naphthyl)cyclohexanecarbonitrile. The distilled yield was 109.8 g (73%) as a colorless liquid that solidified upon standing: bp 190°–200° C. (0.7 mmHg); $^1$H NMR (CDCl$_3$) $\delta$8.80–8.26 (br m, 1H, ArH), 8.05–7.05 (br m, 6H, ArH), 2.80–2.34 (br m, 2H, cyclic-CH$_2$), 2.16–1.60 (br m, 8H, cyclic-CH$_2$).

EXAMPLE 2

Preparation of 1-Arylcycloalkane-1-carboxylic Acid

This example illustrates the preparation of the carboxylic acids (4) from arylcycloalkanecarbonitriles (3).

1-Phenylcyclohexanecarbonitrile (48 g, 259 mmol) was added to a mixture of 240 ml of 2-hydroxyethyl ether and 300 ml of 40% aqueous KOH, forming a heterogeneous solution. The resulting mixture was heated to reflux (T$_{BATH}$=150° C.) for 16 hours. After cooling for 1 hour, the now homogeneous solution was poured into 2 l water and extracted 4 times with diethylether. The aqueous layer was acidified to pH 1 by addition of concentrated aqueous HCl and extracted four times with ethyl acetate. The combined EtOAc extracts were dried over Na$_2$SO$_4$ and the solvents removed under vacuum. Flash chromatography on silica gel eluting with CH$_2$Cl$_2$, followed by recrystallization from EtOAc/hexane, provided 42.03 g (81%) of the desired acid as a yellowish-white, powdery solid: mp 121°–123° C., $^1$H NMR (CDCl$_3$) $\delta$10.97 (br s, 1H, CO$_2$H), 7.27 (m, 5H, ArH), 2.40 (br m, 2H, cyclic-CH$_2$), 1.59 (br m, 8H, cyclic-CH$_2$).

EXAMPLE 3

Preparation of Polyalkylaminoalkyl 1-Arylcycloalkyl-1-carboxylate Salts

A 1-phenylcycloalkane-1-carboxylic acid (4) was dissolved in SOCl$_2$ (2.5 equiv.) and heated (T$_{BATH}$=70° C.) for 16 hours. Excess SOCl$_2$ was removed under aspirator vacuum, and the resulting golden-yellow oil was flushed with Argon for 1 hour. The crude semi-crystalline oil was dissolved in methylene chloride (5 ml/g acid) containing triethylamine (1.1 equiv.), and the dialkylaminoethanol (1.04 equiv.) was added slowly. Typically, a precipitate began forming within 5–10 minutes. After the solution was stirred for 16 hours at room temperature, it was diluted with methylene chloride (30 ml/g acid) and washed once with 0.5 aqueous KOH; the solvents were removed under reduced pressure. The resulting orange oil was flash-chromatographed on silica gel eluting with EtOAc. The running band was collected, freed of solvent, dissolved in Et$_2$O, and converted to the hydrochloride salt by bubbling HCl through the solution. The precipitate was then collected and recrystallized from ethanol/ethyl acetate.

Similarly, other pharmaceutically acceptable salts are prepared by substituting any of the acids named in the Definitions for hydrochloric acid.

Following compounds were prepared by the above procedure.

2-(Dimethylamino)ethyl 1-phenylcyclohexane-1-carboxylate hydrochloride (19). The recrystallized yield was 15.24 g (50%) as a white, powdery solid: mp 178°–179° C.; huH NMR (CDCl$_3$) δ7.32 (s, 5H, ArH), 4.60 (m, 2H, OCH$_2$), 3.15 (br m, 2H, CH$_2$N), 2.42 (m, 6H & 2H, CH$_3$ & cyclic-CH$_2$), 2.10–1.20 (br m, 8H cyclic-CH$_2$).

2-(1-Pyrrolidino)ethyl 1-phenylcyclohexane-1-carboxylate hydrochloride (8). The recrystallized yield was 16.04 g (48%) as a tan flocculent crystalline solid: mp 166°–167.5° C., $^1$H NMR (CDCl$_3$) δ7.31 (s, 5H, ArH), 4.60 (m, 2H, OCH$_2$), 3.67–2.98 (br m, 4H, CH$_2$N and cyclic-CH$_2$), 2.71–1.20 (br m, 16H, cyclic-CH$_2$).

2-(1-Piperidino)ethyl 1-phenylcyclohexane-1-carboxylate hydrochloride (3). The recrystallized yield was 5.30 g (40%) as a white crystalline solid: mp 200°–202° C.; $^1$H NMR (CDCl$_3$) δ12.13 (s, 1H, NH), 7.36 (m, 5H,ArH), 4.61 (m, 2H, OCH$_2$), 3.09 (m, 4H, CH$_2$ and cyclic-CH$_2$), 2.80–0.80 (br, m 18H, cyclic-CH$_2$).

2-(Diethylamino)ethyl 1-phenylcyclohexane-1-carboxylate hydrochloride (15). The recrystallized yield was 5.40 g (41%) as white crystalline solid: mp 160°–160° C.; $^1$H NMR (CDCl$_3$) δ12.28 (s, 1H, NH), 7.32 (m, 5H, ArH), 4.58 (t, 2H, OCH$_2$), 3.18 (q, 2H, CH$_2$), 2.78 (m, 4H, CH$_2$), 2.78–1.33 (br m, 10H, cyclic-CH$_2$), 1.18 (t, 6H, CH$_3$).

2-(4-Morpholino)ethyl 1-phenylcyclohexane-1-carboxylate hydrochloride (12). The recrystallized yield was 9.30 g (30%) as a white crystalline solid: mp 184°–186° C.; $^1$H NMR (CDCl$_3$) δ12.93 (s, 1H, NH), 7.37 (m, 5H, ArH), 4.69 (m, 2H, OCH$_2$), 3.92 (m, 4H, cyclic-OCH$_2$).

2-(2-Pyridino)ethyl 1-Phenylcyclohexane-1-carboxylate Hydrochloride. The recrystallized yield was 5.20 g (53%) as a white crystalline solid: mp 135°–137° C.; $^1$H NMR (CDCl$_3$) δ 8.67 (d, 1H, ArH), 7.99 (m, 2H, ArH), 7.32 (s, 5H, ArH), 6.92 (t, 1H, ArH), 4.60 (t, 2H, OCH$_2$), 3.51 (t, 2H, CH$_2$), 2.30 (m, 2H, cyclic-CH$_2$), 1.90–0.95 (br m, 8H, cyclic-CH$_2$).

2-(1-Piperidino)ethyl 1-Phenylcyclopentane-1-carboxylate hydrochloride. The recrystallized yield was 19 1 g (43%) as a white crystalline solid: mp 167°–168° C.; 1H NMR (CDCl$_3$) δ12.22 (br s, 1H, NH), 7.29 (s, 5H, ArH), 4.51 (t, 2H, OCH$_2$), 3.06 (M, 4H, cyclic-CH$_2$) 2,57 (m, 2H, CH$_2$), 2.35–1.30 (br m, 14H, cyclic-CH$_2$).

2-(2-Pyridino)ethyl 1-Phenylcyclopentane-1-carboxylate hydrochloride. The recrystallized yield was 20.2 g (46%) as a white crystalline solid: mp 143°–145° C., $^1$H NMR (CDCl$_3$) δ 8.59 (m, 1H, ArH), 7.74 (m, 2H, ArH), 7.23 (s, 5H, ArH), 6.82 (m, 1H, ArH), 4.51 (t, 2H, CH$_2$) 3.46 (t, 2H, CH$_2$) 2.56 (m, 2H, CH$_2$), 2.20–1.46 (br m, 6H, cyclic-CH$_2$).

2-(4-Morpholino)ethyl 1-Phenylcyclopentane-1-carboxylate hydrochloride. The recrystallized yield was 11.2 g (51%) as a white crystalline solid: mp 165°–167° C.;$^1$H NMR (CDCl$_3$) δ 13.00 (br m, 1H, NH), 7.29 (s, 5H, ArH), 4.55 (m, 2H, OCH$_2$), 3.89 (m, 4H, cyclic-OCH$_2$), 3.08 (m, 4H, cyclic-OCH$_2$), 2.85–1.40 (br m, 10H, CH$_2$ and cyclic-CH$_2$).

2-(1-Pyrrolidino)ethyl 1-Phenylcyclopropane-1-carboxylate hydrochloride (47). The recrystallized yield was 14.9 g (42%) as a white, crystalline solid: mp 110°–112° C.; $^1$H NMR (CDCl$_3$) δ 12.87 (br s, 1H, NH), 7.36 (m, 5H, ArH), 4.56 (m, 2H, OCH$_2$) 3.65–3.02 (br m, 4H, CH$_2$ and cyclic-CH$_2$), 2.70–1.74 (br m, 6H, cyclic-CH$_2$), 1.61 (m, 2H, cyclopropyl-CH$_2$), 1.29 (m, 2H, cyclopropyl-CH$_2$).

2-(Dimethylamino)ethyl 1-Phenylcyclopropane-1-carboxylate hydrochloride. The recrystallized yield was 20.7 g (62%) as a white crystalline solid; mp 132°–133° C., $^1$H NMR (CDCl$_3$) δ12.38 (br s, 1H, NH), 7.35 (M, 5H, ArH), 4.55 (m, 2H, OCH$_2$), 3.26 (m, 2H, CH$_2$), 2.58 (d, 6H, CH$_3$), 1.62 (m, 2H, cyclopropyl-CH$_2$), 1.28 (m, 2H, cyclopropyl-CH$_2$).

2-(Diethylamino)ethyl 1-Phenylcyclopropane-1-carboxylate hydrochloride. The recrystallized yield was 18.4 g (51%) as a white crystalline solid: mp 126°–128° C.; $^1$H NMR (CDCl$_3$) δ12.38 (br s, 1H, NH), 7.38 (m, 5H, ArH), 4.59 (m, 2H, OCH$_2$), 3.21 (M, 2H, CH$_2$), 2.90 (m, 4H, CH$_2$), 1.65 (m, 2H, cyclopropyl-Ch$_2$), 1.30 m, 2H, cyclopropyl-CH$_2$), 1.20 (t, 6H, CH$_3$).

2-(2-Pyridino)ethyl 1-Phenylcyclopropane-1-carboxylate hydrochloride. The recrystallized yield was 9.9 g (54%) as a white crystalline solid: mp 106°–108° C.; $^1$H NMR (CDCl$_3$) δ 8.70 (d, 1H, Pyr-H), 8.30–7.66 (m, 2H, Pyr-H), 7.33 (s, 5H ArH), 7.11 (d, 1H, Pyr-H), 4.50 (t, 2H, OCH$_2$, 3.49 (t, 2H, CH$_2$), 1.56 (m, 2H, cyclopropyl-CH$_2$), 1.20 (m, 2H, cyclopropyl-CH$_2$).

2-(4-Morpholino)ethyl 1-Phenylcyclopropane-1-carboxylate hydrochloride. The recrystallized yield was 10.0 g (53%) as a white crystalline solid: mp 158°–160° C.; $^1$H NMR (CDCl$_3$) δ12.94 (br s, 1H, NH), 7.39 (m, 5H, ArH), 4.60 (m, 2H, OCH$_2$), 4.30–3.54 (br m, 4H, cyclic-OCH$_2$), 3.4–2.92 (br m, 4H, NCH$_2$), 2.86–2.30 (br m, 2H, cyclic-NCH$_2$), 1.60 (m, 2H cyclopropyl-CH$_2$), 1.28 (m, 2H, cyclopropyl-CH$_2$).

3-(Dimethylamino)propyl 1-Phenylcyclopropane-1-carboxylate hydrochloride. The recrystallized yield was 8.2 g (53%) as a white crystalline solid: mp 141°–142° C.; $^1$H NMR (CDCl$_3$) δ 12.09 (br s, 1H, NH), 7.35 (m, 5H, ArH), 4.12 (t, 2H, OCH$_2$), 2.86 (m, 2H, NCH$_2$), 2.71 (d, 6H, NCH$_3$), 2.14 (m, 2H, CH$_2$), 1.59 (m, 2H, cyclopropyl-CH$_2$), 1.21 (m, 2H, cyclopropyl-CH$_2$).

EXAMPLE 4

SIGMA AND PCP RECEPTOR BINDING ASSAYS

This example illustrates testing of compounds in receptor binding assays.

Frozen brains from male Hartley guinea-pigs were obtained from Pel-Freeze (Rogers, Arkansas). Comparative examination of frozen with fresh brains indicates that results obtained from the commercial frozen brains were the same as those obtained from fresh brains.

The brains plus cerebella were homogenized in 10 volumes (v/w) of 0.1M, pH 7.4, ice-cold Tris-HCl buffer with a Brinkmann polytron at setting 4 for 20 seconds. The homogenates were centrifuged at 20,000×g for 20 minutes at 4° C. The pellets were suspended in 10 volumes of ice-cold water and, after sitting on ice for 10 minutes, were centrifuged 30 minutes at 20,000×g at 4° C. The resulting pellets were resuspended in the above Tris buffer in ratio 1:100 (w/v) for σ receptor assays or in 5 mM Tris-HCl having pH 7.4, for PCP receptor assays. The final suspension was homogenized with a dounce glass-glass tissue grinder Wheaton "200", at small clearance (B), with three strokes before use. Two milliter aliquots of the brain membrane preparation, containing 1.7 mg of protein, were incubated in quadruplicate for one hour at 23° C. with competing mixture of ligand and radioligand. For σ receptors, [$^3$H]-d-SKF-10,047, 2 nM was used. For PCP receptors, [$^3$H] TCP [$^3$H]-1-[1-(2-thienyl)cyclohexyl]piperidine), 1 nM was used. The nonspecific bindings were defined by 0.1 mM d-SKF-10,047 and 0.1 mM phencyclidine respectively for σ and PCP receptors. After incubation, free ligand was separated from bound ligand by rapid filtration through Whatman GF/C filters. The filters had been soaked before use in isoamyl alcohol-saturated water to prevent nonspecific [$^3$H]-d-SKF-10,047 binding to the filter. In the PCP receptor assay, the filter was soaked in 0.5% polyethylenimine to reduce the filter binding of [$^3$H]-TCP. After filtration, the trapped tissue was washed three times with 4 ml aliquots of 0.1 M ice-cold Tris buffer at pH 7.4 for σ receptors and 5 mM, ice-cold Tris buffer pH 7.4 for PCP receptors. The filters were transferred to 5 ml of liquid scintillation fluid and the retained radioactivity was measured by liquid scintillation spectrometry.

EXAMPLE 5

DOPAMINE, 5-HYDROXYTRYPTAMINE, ACETYLCHOLINE, $a_1$- AND $\beta$-ADRENOCEPTOR RECEPTOR ASSAYS This example illustrates the testing of compounds of this invention in dopamine D2, 5-HT$_2$, muscarinic acetylcholine, $a_1$-adrenoceptor and $\beta$-adrenoceptor receptor assays. The receptor assay methods are described in *Eur. J. Pharmacol.*, 155:345 (1988) except that in the $\beta$-adrenoceptor assay, [$^{125}$I]-pindolol was used instead of [$^3$H] dihydroalprenolol.

In this study, guinea-pig brains were used for binding studies. Homogenization and centrifugation procedures for preparation of brain membranes for each receptor assay were the same as described in Example 4 for the σ and PCP receptors. However, brain regions, tissue contents, and buffers may differ depending on the assay. Conditions of binding assays for various receptors were as follows:

For dopamine D$_2$ assay, 3H-spiroperidol (0.15 nM) was incubated in a 2 ml assay (50 mM Tris-HCl, pH 7.4) for 2 hours at 23° C. with membranes from 12 mg of cerebral cortical tissue.

For muscarinic acetylcholine assay, nM) [$^3$H]-quinuclidinyl benzylate ([$^3$H]-QNB) was incubated in a 2 ml assay (50 mM Tris-HCl, pH 7.4) for 2 hours at 23° C. with membranes from 2 mg of whole brain minus cerebellum.

For $a_1$-adrenoceptor assay, [$^3$H]-prazosin (0.4 nM) was incubated in a 1 ml assay (50 mM Tris-HCl, pH 7.4) for 1 hour at 23° C. with membranes from 1 mg of whole brain minus cerebellum.

For $\beta$-adrenoceptor, [$^{125}$I]-pindolol (0.05 nM) was incubated in a 1 ml assay (50 mM Tris-HCl, pH 7.4) for 1 hr at 23° C. with membranes from 1 mg of whole brain minus cerebellum.

Filtration and washing conditions were the same as described above for the σ receptor assay. Nonspecific binding for each receptor was defined by the inclusion of 1 μM haloperidol for dopamine D2, 1 μM haloperidol for 5-HT$_2$, 10 μM scopolamine for muscarinic acetylcholine, 10 μM prazosin for $a_1$-adrenoceptor, and 0.2 μM 1-propranolol for $\beta$-adrenoceptor. Retained radioactivity was measured by liquid scintillation spectrometry except for $^{125}$I-pindolol which was measured by the LKB gamma counter.

IC50 values corresponding to concentrations required to inhibit 50% of radioligand binding to receptors and slopes of the dose response curves were calculated by using the EBDA program [Comp. Programs in Biomed. 17:107 (1983)].

TABLE 1

| NUMBER | R$_3$ | Ar | X | m | n | R$_1$ | R$_2$ | SIGMA RECEPTOR IC50 (nM) | SLOPE | PCP RECEPTOR IC50 (nM) | SLOPE |
|---|---|---|---|---|---|---|---|---|---|---|---|
| 1 | Piperidine | Phenyl | H | 0 | 3 | H | H | 7,783 ± 686 (5) | 0.95 ± 0.12 | 45 ± 5 (5) | 0.78 ± 0.02 |
| 2 | | | None | 1 | 3 | H | H | 104 ± 24 (3) | 0.66 ± 0.1 | 1,832 ± 263 (3) | 0.84 ± 0.02 |
| 3 | | | C(O)O | 2 | 3 | H | H | 24 ± 7 (5) | 0.45 ± 0.04 | 34,890 ± 2,754 (2) | |
| 4 | —CH$_3$ | | C(O)O | 2 | 3 | H | H | >25,000 | | >25,000 | |
| 5 | Pyrrolidine | Phenyl | None | 0 | 3 | H | H | 7,726 ± 781 (3) | 0.83 ± 0.06 | 110 ± 6 (5) | 0.84 ± 0.04 |
| 6 | | | None | 1 | 3 | H | H | 4,739 ± 1426 | 0.88 ± 0.07 | 1,267 ± 96 (3) | 0.85 ± 0.04 |
| 7 | | | None | 2 | 3 | H | H | 141 ± 42·(3) | 1.22 ± 0.03 | 1,718 ± 277 (3) | 0.71 ± 0.08 |
| 8 | | | C(O)O | 2 | 3 | H | H | 5.1 ± 1.7 (3) | 0.50 ± 0.02 | 64,730 ± 458 (2) | |
| 9 | —CH$_3$ | | C(O)O | 2 | 3 | H | H | 242 ± 123 (3) | 0.62 ± 0.18 | >25,000 | |
| 10 | Morpholine | Phenyl | None | 0 | 3 | H | H | 2531 ± 457 (6) | 0.47 ± 0.02 | 633 ± 71 (5) | 0.93 ± 0.03 |
| 11 | | | None | 1 | 3 | H | H | 710 ± 68 (3) | 0.60 ± 0.03 | >25,000 | |
| 12 | | | C(O)O | 2 | 3 | H | H | 44 ± 7 (5) | 0.48 ± 0.05 | >100,000 | |
| 13 | Diethylamine | Phenyl | None | 0 | 3 | H | H | 573 ± 124 (3) | 0.40 ± 0.07 | 331 ± 34 (5) | 0.96 ± 0.01 |
| 14 | | | None | 1 | 3 | H | H | 208 ± 85 (3) | 0.66 ± 0.17 | >25,000 | |
| 15 | | | C(O)O | 2 | 3 | H | H | 30 ± 5 (3) | 0.66 ± 0.16 | 40,858 ± 4,474 (2) | |
| 16 | —CH$_3$ | | C(O)O | 2 | 3 | H | H | 2,226 ± 289 (3) | 0.86 ± 0.07 | >25,000 | |
| 17 | Dimethyl | Phenyl | None | 0 | 3 | H | H | 1,950 ± 332 (5) | 0.53 ± 0.05 | 242 ± 8 (4) | 0.81 ± 0.01 |
| 18 | amine | | None | 1 | 3 | H | H | 4,130 ± 235 (3) | 0.85 ± 0.07 | >25,000 | |
| 19 | | | C(O)O | 2 | 3 | H | H | 9.2 ± 0.8 (3) | 0.54 ± 0.02 | 21,708 ± 1938 (3) | |
| 20 | —CH$_3$ | | C(O)O | 2 | 3 | H | H | 12,316 ± 3,442 (3) | 1.22 ± 0.15 | >25,000 | |

TABLE 2

| NUMBER | R3 | Ar | R1 | R2 | n | m | X | SIGMA RECEPTOR IC50 (nM) | SLOPE | PCP RECEPTOR IC50 (Nm) | SLOPE |
|---|---|---|---|---|---|---|---|---|---|---|---|
| 2 | Piperidine | Phenyl | None | H | 3 | 1 | None | 104 ± 24 (3) | 0.66 ± 0.1 | 1,832 ± 263 (3) | 0.84 ± 0.02 |
| 21 | | | 3-OH | H | 3 | 1 | None | >25,000 | | >25,000 | |
| 23 | | | 4-CH3 | H | 3 | 1 | None | 223 ± 76 (3) | 0.69 ± 0.01 | >25,000 | |
| 24 | | | 4-NO2 | H | 3 | 1 | None | 249 ± 108 (3) | 0.47 ± 0.06 | >25,000 | |
| 25 | | | 3-Cl | H | 3 | 1 | None | 71 ± 13 (3) | 0.69 ± 0.05 | 1,834 ± 355 (3) | 0.84 ± 0.05 |
| 26 | | | 3-OCH3 | H | 3 | 1 | None | 326 ± 117 (3) | 0.74 ± 0.07 | >25,000 | |
| 27 | | | 4-OCH3 | H | 3 | 1 | None | 221 ± 50 (3) | 0.69 ± 0.04 | >25,000 | |
| 28 | | | 3-OCH3 | 4-OCH3 | 3 | 1 | None | 387 ± 18 | 0.56 ± 0.03 | >25,000 | |
| 6 | Pyrrolidine | Phenyl | H | H | 3 | 1 | None | 4,749 ± 1426 (3) | 0.88 ± 0.07 | 1,267 ± 96 (3) | 0.85 ± 0.04 |
| 29 | | | 3-OH | H | 3 | 1 | None | 1,082 ± 106 (3) | 0.80 ± 0.07 | 1,322 ± 119 (3) | 0.79 ± 0.02 |
| 30 | | | 4-OH | H | 3 | 1 | None | 1,735 ± 293 (3) | 0.78 ± 0.02 | >25,000 | |
| 31 | | | 4-NO2 | H | 3 | 1 | None | 282 ± 65 (3) | 0.65 ± 0.05 | >25,000 | |
| 32 | | | 3-Cl | H | 3 | 1 | None | 248 ± 39 (3) | 0.73 ± 0.16 | 867 ± 9 (3) | 1.78 ± 0.09 |
| 33 | | | 3-OCH3 | H | 3 | 1 | None | 1,189 ± 192 (3) | 0.73 ± 0.08 | 552 ± 20 (3) | 0.89 ± 0.08 |
| 34 | | | 4-OCH3 | H | 3 | 1 | None | 546 ± 54 (3) | 0.80 ± 0.07 | >25,000 | |
| 35 | | | 3-OCH3 | 4-OCH3 | 3 | 1 | None | 1,317 ± 167 (3) | 0.66 ± 0.07 | >25,000 | |
| 11 | Morpholine | Phenyl | None | H | 3 | 1 | None | 710 ± 68 (3) | 0.60 ± 0.03 | >25,000 | |
| 36 | | | 3-OH | H | 3 | 1 | None | >25,000 | | >25,000 | |
| 37 | 7 | | 3-OCH3 | H | 3 | 1 | None | >25,000 | | >25,000 | |
| 38 | | | 3-OCH3 | 4-OCH3 | 3 | 1 | None | >25,000 | | >25,000 | |
| 14 | Diethyl Amine | Phenyl | None | H | 3 | 1 | None | 208 ± 85 (3) | 0.66 ± 0.17 | >25,000 | |
| 39 | | | 4-NO2 | H | 3 | 1 | None | 304 ± 140 (3) | 0.44 ± 0.01 | >25,000 | |
| 18 | Dimethyl Amine | Phenyl | None | H | 3 | 1 | None | 4,130 ± 235 (3) | 0.85 ± 0.07 | >25,000 | |
| 40 | | | 3-OH | H | 3 | 1 | None | 10,054 ± 1,118 (3) | 0.61 ± 0.01 | >25,000 | |
| 41 | | | 4-CH3 | H | 3 | 1 | None | 541 ± 70 (3) | 0.62 ± 0.03 | >25,000 | |
| 42 | | | 3-OCH3 | H | 3 | 1 | None | 2,851 ± 1,034 (3) | 0.70 ± 0.06 | >25,000 | |
| 43 | | | 3-OCH3 | 4-OCH3 | 3 | 1 | None | 9,049 ± 1,313 (3) | 0.66 ± 0.13 | >25,000 | |

| NUMBER | R3 | Ar | X | R1 | R2 | n | m | SIGMA RECEPTOR IC50 (nM) | SLOPE | PCP RECEPTOR IC50 (Nm) | SLOPE |
|---|---|---|---|---|---|---|---|---|---|---|---|
| 2 | Piperidine | Phenyl | None | H | H | 3 | 1 | 104 ± 24 (3) | 0.66 ± 0.01 | 1,832 ± 263 (3) | 0.84 ± 0.02 |
| 44 | | | None | H | H | 2 | 1 | 995 ± 214 (3) | 1.03 ± 0.04 | >25,000 | |
| 45 | | | None | H | H | 0 | 1 | 5,589 ± 214 (3) | 0.83 ± 0.19 | 8,844 ± 90 (3) | 0.83 ± 0.03 |
| 6 | Pyrrolidine | Phenyl | C(O)O | H | H | 3 | 2 | 44 ± 7 (5) | 0.48 ± 0.05 | >25,000 | |
| 46 | | | C(O)O | H | H | 2 | 2 | 454 ± 80 (3) | 0.68 ± 0.06 | >25,000 | |
| 47 | | | C(O)O | H | H | 0 | 2 | 1,463 ± 102 (3) | 0.78 ± 0.09 | >25,000 | |

TABLE 4

| NUMBER | SIGMA | PCP | DOPAMINE D2 | MUSCARINIC ACETYLCHOLINE | 5-HT2 | α1-ADRENOCEPTOR | β-ADRENOCEPTOR |
|---|---|---|---|---|---|---|---|
| 3 | 26 ± 7 | 34,890 ± 2,754 | 5,957 ± 640 | 46 ± 7 | 3,657 ± 483 | 24,084 ± 750 | 80,428 ± 5,245 |
| 8 | 5.1 ± 1.7 | 64,730 ± 458 | 7,598 ± 1,675 | 123 ± 16 | 2,929 ± 536 | 23,205 ± 4,404 | 85,000 ± 5,234 |
| 12 | 44 ± 7 | >100,000 | 55,702 ± 3,668 | 13,953 ± 803 | 18,748 ± 959 | >100,000 | >200,000 |
| 15 | 30 ± 5 | 40,858 ± 4,474 | 12,074 ± 3,919 | 189 ± 35 | 2,185 ± 69 | 30,094 ± 10,191 | 81,888 ± 4,656 |
| 19 | 9.2 ± 0.8 | 21,708 ± 1,938 | 12,220 ± 2,327 | 750 ± 36 | 1,415 ± 522 | 28,998 ± 6,468 | 85,666 ± 2,333 |

What is claimed is:

1. A compound of the formula (I)

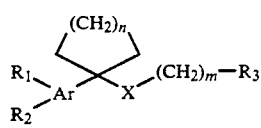

and its pharmaceutically acceptable salts, wherein
Ar is aryl;
$R_1$ and $R_2$ are independently selected from the group consisting of hydrogen, hydroxy, lower alkyl, cycloalkyl, alkoxy, nitro, thio or halo;
$R_3$ is morpholine;
X is zero, ester, ether, ketone, amide, thioketone, thioamide, thioether or thioester;
n is 2, 3, 4 or 5; and
m is zero, 1, 2, 3, 4 or 5.

2. The compound of claim 1 wherein aryl is phenyl.

3. The compound of claim 2 wherein X is zero, ester, ether or ketone.

4. The compound of claim 3 wherein n is 2, 3 or 4.

5. The compound of claim 4 wherein m is zero, 1, 2 or 3.

6. The compound of claim 5 wherein $R_1$ is lower alkyl, alkoxy or nitro and $R_3$ is hydrogen or alkoxy.

7. The compound of claim 6 wherein X is ester.

8. The compound of claim 7 wherein $R_3$ is morpholine, x is carboxyl, m is 2, n is 3 and $R_1$ and $R_2$ are both hydrogen, namely 2-(4-morpholine)ethyl 1-phenylcyclohexane-1-carboxylate.

9. The compound of claim 7 wherein X is zero, m is 1, n is 3 and $R_1$ and $R_2$ are both hydrogen, namely 2-(4-morpholine) methly-1-phenyl-cyclohexane.

10. A method of treatment of diseases caused by sigma receptor dysfunction comprising administering to a person in need of such treatment a therapeutically effective amount of the compound of formula (I)

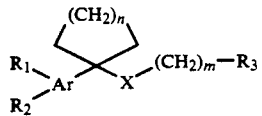

and its pharmaceutically acceptable salts, wherein
Ar is aryl;
$R_1$ and $R_2$ are independently selected from the group consisting of hydrogen, hydroxy, lower alkyl, cycloalkyl, alkoxy, nitro, thio or halo;
$R_3$ is morpholine;
X is zero, ester, ether, ketone, amide thioketone, thioamide, thioether or thioester;
n is 2, 3, 4 or 5; and
m is zero 1, 2, 3, 4 or 5.

11. The method of claim 10 wherein the disease caused by sigma receptor dysfunction is psychosis, arrhythmia, stroke, convulsions, ischemia or dementia.

12. The method of claim 11 wherein aryl is phenyl; X is zero, ester, ether or ketone; n is 2, 3 or 4; m is zero, 1, 2 or 3; $R_1$ is lower alkyl, alkoxy or nitro; and $R_2$ is hydrogen or alkoxy.

13. The method of claim 12, wherein X is carboxyl, m is 2, n is 3, and $R_1$ and $R_2$ are both hydrogen.

14. The method of claim 12 wherein X is zero, m is 1 and n is 3 and $R_1$ and $R_2$ are both hydrogen.

15. The method of claim 13 wherein the disease is psychosis.

16. The method of claim 13 wherein the disease is arrhythmia.

17. The method of claim 13 wherein the disease are convulsions.

18. The method of claim 13 wherein the disease is stroke.

19. The method of claim 13 wherein the disease is dementia.

20. The method of claim 13 wherein the disease is ischemia.

* * * * *